(12) United States Patent
Holsworth

(10) Patent No.: US 11,291,730 B2
(45) Date of Patent: Apr. 5, 2022

(54) COMPOSITIONS AND METHODS FOR WOUND TREATMENT

(71) Applicant: Eluciderm Inc., San Diego, CA (US)

(72) Inventor: Daniel D Holsworth, San Diego, CA (US)

(73) Assignee: ELUCIDERM INC., San Diego, CA (US)

( * ) Notice: Subject to any disclaimer, the term of this patent is extended or adjusted under 35 U.S.C. 154(b) by 0 days.

(21) Appl. No.: 16/153,753

(22) Filed: Oct. 6, 2018

(65) Prior Publication Data

US 2019/0105398 A1    Apr. 11, 2019

Related U.S. Application Data

(60) Provisional application No. 62/684,439, filed on Jun. 13, 2018, provisional application No. 62/569,025, filed on Oct. 6, 2017.

(51) Int. Cl.

| | | |
|---|---|---|
| *A61P 17/02* | (2006.01) | |
| *A61K 47/36* | (2006.01) | |
| *A61K 31/519* | (2006.01) | |
| *A61K 47/10* | (2017.01) | |
| *A61L 15/44* | (2006.01) | |
| *A61L 15/28* | (2006.01) | |
| *A61K 9/70* | (2006.01) | |
| *A61L 26/00* | (2006.01) | |
| *A61K 35/00* | (2006.01) | |
| *A61L 17/00* | (2006.01) | |
| *A61K 9/06* | (2006.01) | |
| *A61K 9/00* | (2006.01) | |
| *A61K 47/02* | (2006.01) | |

(52) U.S. Cl.
CPC ............ *A61K 47/36* (2013.01); *A61K 9/7023* (2013.01); *A61K 31/519* (2013.01); *A61K 35/00* (2013.01); *A61K 47/10* (2013.01); *A61L 15/28* (2013.01); *A61L 15/44* (2013.01); *A61L 17/005* (2013.01); *A61L 26/0023* (2013.01); *A61L 26/0066* (2013.01); *A61P 17/02* (2018.01); *A61K 9/0014* (2013.01); *A61K 9/06* (2013.01); *A61K 47/02* (2013.01); *A61L 2300/412* (2013.01)

(58) Field of Classification Search
None
See application file for complete search history.

(56) References Cited

U.S. PATENT DOCUMENTS

| | | | | |
|---|---|---|---|---|
| 4,568,343 A | * | 2/1986 | Leeper ................. | A61K 9/0014 424/449 |
| 4,649,075 A | * | 3/1987 | Jost ..................... | A61K 9/7084 428/305.5 |
| 5,340,586 A | * | 8/1994 | Pike .................... | A61K 9/1647 424/426 |
| 2004/0202665 A1 | * | 10/2004 | Lazarovits ........ | A61K 39/39541 424/178.1 |
| 2006/0051384 A1 | * | 3/2006 | Scholz ................ | A61K 36/61 424/405 |
| 2007/0053968 A1 | * | 3/2007 | Tatapudy ............. | A61K 31/138 424/449 |
| 2007/0135444 A1 | * | 6/2007 | Capdeville .......... | A61K 31/506 514/252.18 |
| 2007/0219257 A1 | | 9/2007 | Beachy et al. | |
| 2010/0267626 A1 | | 10/2010 | Cheung et al. | |
| 2012/0318262 A1 | | 12/2012 | Lee et al. | |
| 2015/0231266 A1 | | 8/2015 | Metcalfe et al. | |
| 2017/0128271 A1 | | 5/2017 | Freer et al. | |

FOREIGN PATENT DOCUMENTS

| | | |
|---|---|---|
| CN | 105288695 | 2/2016 |
| WO | WO 2017/173026 A1 | 10/2017 |

OTHER PUBLICATIONS

Vangipuram et al., Wnt pathway activity confers chemoresistance to cancer stem-like cells in a neuroblastoma cell line, Tumor Biol. (2012) 33:2173-2183 (Year: 2012).*
Wu et al., Hyaluronic acid conjugated graphene oxide for targeted drug delivery, C A R B O N 6 9 ( 2 0 1 4 ) 3 7 9-3 8 9 (Year: 2014).*
Sigma-Aldrich, Phosphate Buffered Saline, https://www.sigmaaldrich.com/catalog/product/sigma/p5119?lang=en&region=US, retrieved online Jan. 28, 2020 (Year: 2020).*
Ran et al., Hyaluronic Acid-Templated Ag Nanoparticles/Graphene Oxide Composites for Synergistic Therapy of Bacteria Infection, ACS Appl. Mater. Interfaces May 2017, 9, 19717-19724 (Year: 2017).*
Olivera Stojadinovic et al. "Molecular Pathogenesis of Chronic Wounds", American Journal of Pathology, vol. 167, No. 1, pp. 59-69, Jul. 2005.
Shih-Min A. Huang et al., "Tankyrase inhibition stabilizes axin and antagonizes Wnt signalling", Nature, vol. 461, pp. 614-620, Oct. 2009.
Zhang et al, "Functional Graphene Oxide as a Nanocarrier for Controlled Loading and Targeted Delivery of Mixed Anticancer Drugs", small, 6, No. 4, 537-544, Feb. 2010.
Anna P. Lam et al., "Beta-catenin signaling: a novel mediator of fibrosis and potential therapeutic target", Current Opinion in Rheumatology 23:562-567, 2011.

(Continued)

*Primary Examiner* — Jennifer A Berrios
(74) *Attorney, Agent, or Firm* — Squire Patton Boggs (US) LLP

(57) ABSTRACT

A composition for treating a wound includes graphene oxide (GO) and hyaluronic acid (HA) that are covalently linked, XAV939, and water. The composition can also include a surfactant, such as PEG. The composition can be topically administered to a subject to treat a wound of the subject. Methods of treating a wound using the composition are also provided.

13 Claims, 2 Drawing Sheets

(56) References Cited

OTHER PUBLICATIONS

G.-Y. Chen et al., "A graphene-based platform for induced pluripotent stem cells culture and differentiation", Biomaterials, 33, 418-427, Oct. 2012.

Bingan Lu et al., "Graphene-based composite materials beneficial to wound healing", The Royal Society of Chemistry Nanoscale, DOI: 10.1039/c2nr11958g, 2012.

Mendes et al., "A Rat Model of Diabetic Wound Infection for the Evaluation of Topical Antimicrobial Therapies", Comparative Medicine, vol. 62, No. 1, pp. 37-48, Feb. 2012.

Tziotzios et al., "Cutaneous scarring: Pathophysiology, molecular mechanisms, and scar reduction therapeutics", J Am Acad Dermatol 66:13-24, Jan. 2012.

Igota et al., "Identification and Characterization of Wnt Signaling Pathway in Keloid Pathogenesis", Int. J Med. Sci. vol. 10, pp. 344-354, Feb. 2013.

Fangyuan Li et al., "Hyaluronic acid-conjugated graphene oxide/photosensitizer nanohybrids for cancer targeted photodynamictherapy", J. Mater. Chem. B, 1, 1678, Mar. 2013.

Radhika P. Atit, "Sustained β-catenin activation in dermal fibroblasts promotes fibrosis by regulating cell proliferation and extracellular matrix protein-coding genes" 2015 (presentation).

Hamburg et al., "Sustained β-catenin activity in dermal fibroblasts promotes fibrosis by up-regulating expression of extracellular matrix protein-coding genes", J Pathol., 235(5): 686-697, Apr. 2015.

Bastakoty et al., "Inhibition of Wnt/beta-catenin pathway promotes regenerative repair of cutaneous and cartilage injury", The FASEB Journal, vol. 29, pp. 1-12, Aug. 2015.

Neuman et al., "Hyaluronic Acid and Wound Healing", J Pharm Pharm Sci, 18(1) 53-60, Jan. 2015.

Eva Garcia-Alegria et al., "Graphene Oxide promotes embryonic stem cell differentiation to haematopoietic lineage", Scientific Reports, 6:25917, May 2016.

Tripp Leavitt et al., "Scarless wound healing: finding the right cells and signals", Cell Tissue Res, 365:483-493, Jun. 2016.

Erika Nishida et al., "Graphene oxide scaffold accelerates cellular proliferative response and alveolar bone healing of tooth extraction socket", International Journal of Nanomedicine 11, 2265-2277, May 2016.

Ho Sang Jung et al., "Nanographene Oxide-Hyaluronic Aid Conjugate for Photothermal Ablation Therapy of Skin Dancer", ACSNANO, vol. 8, No. 1, pp. 260-268, 2014.

International Search Report and Written Opinion on PCT/US18/54776.

Aitzetmuller et al., "Challenges and Opportunities in Drug Delivery for Wound Healing", Regenerative Medicine and Plastic Surgery, pp. 27-38, available online 2019 (Year: 2019).

Bastakoty, "Therapeutic inhibition of the Wnt signaling pathway to promote regenerative repair of tissue injury", May 2016 (Year: 2016).

Thorne et al., "Small-molecule inhibition of Wnt signaling through activation of casein kinase 1α," Nat Chem Biol. 2010, 6(11), 829-836.

Robert L. Wilbur, "The Difference Between Topical and Transdermal Medications," Gensco Pharma, May 2017—genscopharma.com.

ThermoFisher Scientific, Safety Data Sheet, Dimethyl-Sulfoxide, https://www.fishersci.com/store/msds?partNumber=D1391&productDescription=DIMETHYL+SULFOXIDE+GC+HS+1L&vendorId=VN00033897&countryCode=US&language=en, retrieved online Aug. 28, 2021 (Year: 2009).

\* cited by examiner

COMPOSITIONS AND METHODS FOR WOUND TREATMENT

CROSS REFERENCE TO RELATED APPLICATIONS

This application claims priority to U.S. Provisional Application No. 62/569,025, filed Oct. 6, 2017, and to U.S. Provisional Application No. 62/684,439, filed Jun. 13, 2018, the disclosure of each of which is incorporated by reference herein in its entirety.

BACKGROUND

The invention described herein relates to compositions and methods for wound treatment, and in particular, the prevention and/or reduction of scar formation during wound healing.

Wound healing is a complex process, involving an inflammation phase, a granulation tissue formation phase, and a tissue remodeling phase. These events are triggered by cytokines and growth factors that are released at the site of injury. Many factors can complicate or interfere with normal adequate wound healing. Chronic wounds, such as diabetic foot ulcers, venous leg ulcers, and pressure ulcers are particularly troublesome and challenging to treat.

A scar is the mark left in the skin by new connective tissue that replaces tissue which has been injured. Scarring in the skin after trauma, surgery, burn or sports injury can be a medical problem, resulting in loss of function, restriction of tissue movement and adverse psychological effects. Skin fibrosis, an irreversible pathological process that causes a loss of normal tissue structure and organ function, is associated with scarring. While the pathways and processes underlying scar formation have been better understood in the recent years, no effective therapeutic approaches for scar management are available, and there are no prescription drugs for the prevention or treatment of dermal scarring.

Currently available techniques for treating scarring (e.g., silicone sheeting (pressure therapy), topical ointments, resurfacing, peel, dermabrasion, lasers, cryosurgery, bleomycin and 5-fluorouracil injection, excision (revision surgery, radiotherapy), reconstruction possibly with skin grafts, flaps, etc.) focus on improving the aesthetics of existing scars, and have issues related to scarring recurrence and side-effects, such as dermal atrophy and hypopigmentation.

The Wnt pathway has been recently shown to play a key role in dermal fibrosis and scarring. The Wnt pathway is an evolutionary conserved pathway that regulates crucial aspects of cell fate determination, cell polarity, cell migration, neural patterning, and organogenesis during embryonic development. This pathway is instrumental in ensuring proper tissue development in embryos and tissue maintenance in adults. Wnt signaling is involved at the beginning stages of skin development. Following gastrulation, embryonic cells of the ectoderm and the mesoderm differentiate to form the epidermis and dermis, respectively.

Although there are at least three distinct Wnt signaling pathways involved in the signal transduction process, the canonical (or β-catenin dependent) Wnt pathway is the most understood. β-Catenin is the key effector molecule resulting from the signaling of the canonical Wnt pathway, and its protein levels are regulated through a "destruction complex". In the absence of a Wnt signal, the transcriptional activator β-catenin is actively degraded in the cell by the actions of a protein complex, designated the "destruction complex". Within this complex, Axin-1 and -2 with adenomatous polypsis coli form a scaffold that facilitates β-catenin phosphorylation by casein-kinase 19a and glycogen synthase kinase 3β. Phosphorylated β-catenin is recognized and ubiquitinylated, resulting in its proteosomal degradation. Tankryase I and II (TNK1 and 2) are poly(ADP-ribose) polymerases (PARPs) that function to parsylate and destabilize Axin-1 and -2 proteins, thus destabilizing the β-catenin destruction complex. Once the destruction complex is destabilized, this allows β-catenin to be dephosphorylated, and subsequently stabilized and allowed to accumulate in the cytoplasm and enter the cell nucleus, where it interacts with members of the Tcf/Lef family. β-catenin converts the Tcf proteins into potent transcriptional activators by recruiting co-activator proteins, thus ensuring efficient activation of Wnt target genes. The Wnt pathway, once activated by the Wnt family of natural ligands, upregulates TNK1 and 2 to help destabilize the destruction complex. Studies have shown that TNK1 and 2 are critical regulators of canonical Wnt signaling.

Canonical Wnt signaling is over-activated in a variety of tumors where it plays a central role in cell growth and metastasis. In addition, the Wnt pathway has been shown to regulate cell proliferation in the adult epidermis, indirectly impacting the rate and extent of skin wound healing and fibrosis or scarring. Further, the Wnt/β-catenin pathway has been shown to cause overstimulation of dermal fibroblasts, which can give rise to myofibroblasts. Myofibroblasts are endowed with contractile function, which allows them to play a role in extracellular matrix (ECM) fibers to close open wounds. Overexpression of myofibroblasts causes excess collagen and ECM protein secretion, which in turn causes fibrosis and scarring. Sustained β-catenin activity in dermal fibroblasts promotes fibrosis by upregulating expression of ECM protein-coding genes. β-Catenin levels have been shown to regulate wound size and mediate the effect of TGF-β in cutaneous healing. The Wnt/β-catenin pathway has been shown to be upregulated in hypertrophic scars and keloid fibroblasts. Thus, the Wnt/β-catenin pathway induces β-catenin signaling in cutaneous mesenchymal cells, leading to their activation and induction of a sustained fibrotic response.

TNK1 and 2 have been shown to be druggable targets for modulation of the Wnt/β-catenin pathway. However, recently it has been demonstrated that systemic inhibition of TNK1 and 2 can cause intestinal toxicity due to inhibition of intestinal crypt cell renewal, a process primarily driven by the Wnt/β-catenin pathway.

XAV939 is a small molecule that selectively inhibits Wnt/β-catenin-mediated transcription through TNK 1 and 2 inhibition with an IC50 of 11 nM/4 nM in cell-free assays, regulates axin levels, and does not affect CRE, NF-κB, or TGF-β. Recently, topical application of XAV939 in a mouse ear punch assay demonstrated that XAV939 significantly increased rate of wound closure with reduced fibrosis (scarring). However, XAV939 was dissolved in DMSO and used only as a "research tool" compound due to its very low aqueous solubility (<1 mg/mL). The problem with this approach is that humans cannot tolerate the use of DMSO. A soluble form of XAV939 suitable for humans is required for practical and medical use.

SUMMARY OF THE INVENTION

In one aspect of the present invention, a composition for treating a wound is provided. The composition comprises: a matrix component comprising graphene oxide (GO) and hyaluronic acid (HA), wherein the GO and HA are covalently linked via a linker; XAV939; and water. The covalently linked GO and HA is also referred to herein as GO-HA or GO-HA conjugate. The composition can be in the form of a suspension, where the GO-HA can be present in the forms of dispersed microparticles suspended in the water.

In some embodiments, the composition further comprises a surfactant, which can be a polyethylene glycol (PEG). The PEG can have a molecular weight of about 200 to about 400 Daltons. The PEG can be in an amount of from about 0.1 wt % to about 20 wt % of the total composition.

In some embodiments, the composition further comprises a thickener, which for example, can be hydroxypropyl cellulose (HPC).

In some embodiments, the linker linking the GO and HA includes 2-25 carbons. In some embodiments, the linker can be straight-chained (or linear). In other embodiments, the linker can be branched. In some embodiments, the linker comprises a linear alkylene —$C_mH_{2m}$— unit where m can be from 1 to 20. In some other embodiments, the linker can comprise one or more heteroatoms. For example, the linker can include one or more —$CH_2CH_2O$— units. In certain embodiments, the linker comprises —$R^x$—$R^S$—$R^y$—, wherein $R^x$ and $R^y$ are each independently selected from the group consisting of —CO—, —COO—, —NH—, —NH—NH—, —NH—NH—CO—, —CS—, —S—, —O—, and wherein $R^S$ is an unsubstituted or substituted linear alkylene group having 1-40, or 2-20 backbone carbons. In specific embodiments, $R^x$ and $R^y$ are each —NH—NH—CO—.

In some embodiments, the weight ratio of XAV939 to GO-HA can be from about 1:100 to about 100:1, for example, from about 1:2 to about 2:1. In some embodiments, XAV939 constitutes from about 0.001 wt % to about 5 wt % of the total composition. In certain embodiments, the GO-HA constitutes from 0.001 wt % to about 5 wt % of the total composition.

In another aspect, a medical device is provided. The medical device includes a substrate; and the composition(s) described herein which is applied on the substrate. The substrate can be a patch, a pad, a suture, a gauze, a tape, or a bandage.

In a further aspect, a method of treating a cutaneous wound in a subject (a human or non-human animal, such as a mammal) by contacting the wound with an effective amount of the composition(s) as described herein, is provided. The wound can be a surgical wound or a burn. In some embodiments, the wound can be a chronic wound such as an ulcer. In some embodiments, the method further comprises delivering a second wound medication to the subject, the second wound medication comprising one or more of: corticosteroid, a cytotoxic drug, an antibiotic, an antiseptic, nicotine, an anti-platelet drug, an NSAID, colchicine, an anti-coagulant, a vasoconstricting drug or an immunosuppressive, a growth factor, an antibody, a protease, a protease inhibitor, an antibacterial peptide, an adhesive peptide, a hemostatic agent, living cells, honey, or nitric oxide.

In a further aspect, a method of preparing a GO-HA conjugate is provided. The method includes: modifying GO by converting at least some of the benzoxylic acid groups of the GO to terminal aliphatic carboxylic acid groups; derivatizing HA by reacting HA with a reagent having dual functional groups reactive to the terminal aliphatic carboxylic acid groups, the dual functional groups intervened by a spacer group; and reacting the modified GO and the derivatized HA to form the GO-HA conjugate. In some embodiments, the spacer group can comprise a linear alkylene having 2-20 backbone carbons. In some embodiments, the reagent for derivatizing HA is a dihydrazide. In some embodiments, in the GO-HA conjugate, the weight ratio of GO:HA is from about 1:1 to about 1:20, or from about 1:6 to about 1:10.

DETAILED DESCRIPTION

Figure 1:
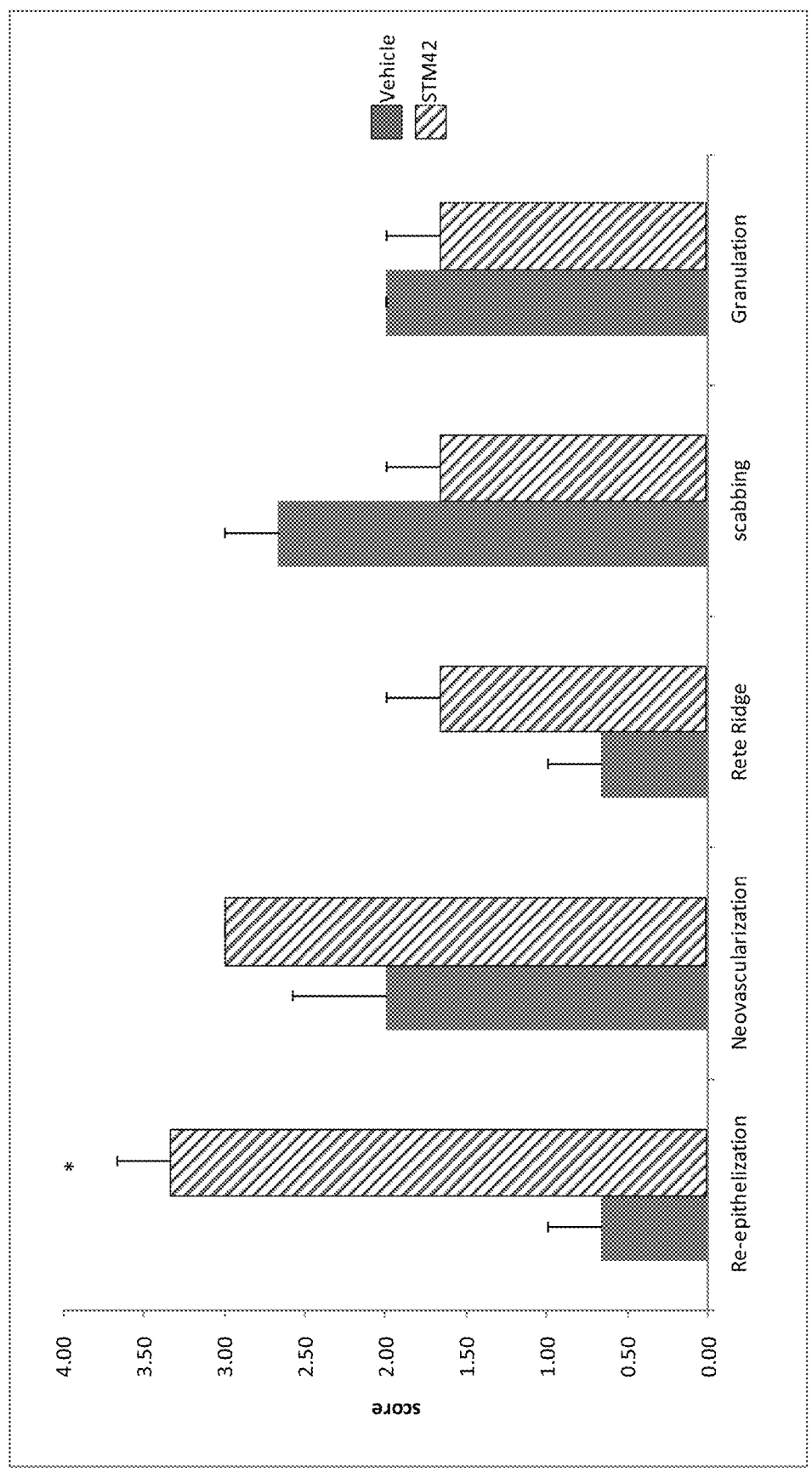
FIG. 1 is a plot showing the effect of a composition of the present invention on scar reduction related to wound healing of an animal model as compared to the effect of a vehicle composition.

In one aspect of the invention, a composition for treating a wound is provided, which includes: a matrix component comprising a conjugate of graphene oxide (GO) and hyaluronic acid (HA) where GO and HA are covalently linked via a linker; XAV939; and water. The covalently-linked GO and HA is also referred to herein as GO-HA conjugate or simply GO-HA.

XAV939 is a potent tankyrase inhibitor, with a chemical name 3,5,7,8-Tetrahydro-2-[4-(trifluoromethyl)phenyl]-4H-thiopyrano[4,3-d]pyrimidin-4-one. The structure of XAV939 is shown below:

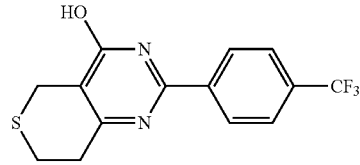 [SMILES: Oc1nc(-c2ccc(C(F)(F)F)cc2)nc2c1CSCC2]

Graphene oxide (GO) as used herein refers to an oxidized form of graphene, which is a single layer form of graphite. GO can be obtained by treating graphite with strong oxidizers. GO contains carbon, oxygen, and hydrogen in various amounts, depending on how it is made. It can have several hundreds of nanometers, up to several micrometers, its planar direction, and about 0.7-1.2 nm in thickness. GO can include various oxygen containing moieties, such as oxygen epoxide groups, carboxylic acid (—COOH), phenol, etc., when prepared using sulphuric acid (e.g. Hummers method). An example GO structure is shown below.

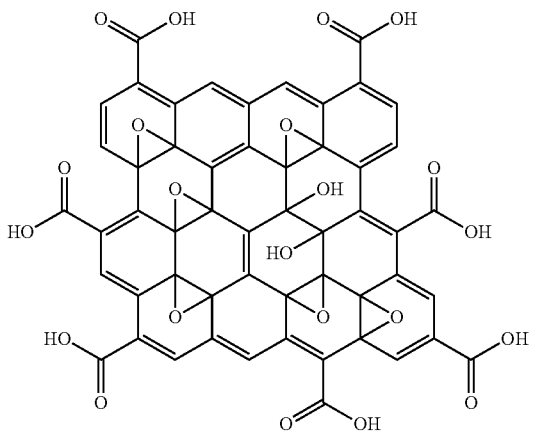

Hyaluronic acid (HA) is an anionic, highly hydrophilic, non-sulfated glycosaminoglycan, occurring naturally throughout the human body. It can be several thousands of carbohydrate units long, and can bind to water giving it a gel of stiff viscous quality. An example structure of HA is provided below:

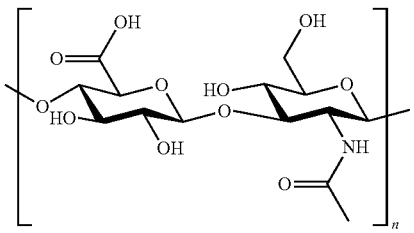

In the composition of present invention, the GO and HA are covalently linked to form a matrix component (or a carrier), which can serve to solubilize XAV939 as well as providing other simultaneous benefits to wound healing. The covalent linking can be accomplished by using a linker (or linker moiety). In some embodiments, the linker can include 2-25 carbons. In some embodiments, the linker is linear. In other embodiments, the linker is branched. The linker can be saturated or unsaturated.

In some embodiments, the linker can comprise a $C_2$-$C_{25}$ alkylene group, where the carbons and hydrogens in the alkylene group can be substituted by oxygen or other atoms or groups such as hydroxy, carboxy, amino, alkyl, alkoxy, alkenyl, alkynyl, nitro, etc. In some embodiments, the linker can comprise one or more —$CH_2CH_2O$— units.

In some embodiments, the linker comprises —$R^x$—$R^S$—$R^y$—, wherein $R^x$ and $R^y$ are each independently selected from the group consisting of —CO—, —COO—, —NH—, —NH—NH—, —NH—NH—CO—, —CS—, —S—, —O—, and wherein $R^S$ (which is also referred to as the spacer group in this application) can be an unsubstituted or substituted, saturated or unsaturated linear alkylene group having 2-20 backbone carbons. In particular embodiments, both $R^x$ and $R^y$ are *—NH—NH—CO— (* denoting the ends of the linker distal to $R^S$).

In some embodiments of the composition, the weight ratio of XAV939 to GO-HA can be from about 1:100 to 100:1, e.g., from about 1:2 to about 2:1. In some embodiments, in the GO-HA conjugate, the weight ratio of GO:HA can be from about 1:1 to about 1:20, or from about 1:6 to about 1:10.

In general, the composition overall can appear as a slightly dark or black viscous liquid. XAV939 is evenly dispersed in the viscous suspension, which is stable at room temperature for months. In some embodiments, the composition further comprises a surfactant that enhances mixability or solubility of hydrophobic substances in water. In some examples, the surfactant can be a non-ionic hydrophilic material such as polyethylene glycol (PEG). The PEG can have a number-averaged molecular weight of from about 100 to about 10,000 Daltons, or about 200 to about 4000 Daltons, e.g., from about 200 to about 1000, from about 200 to about 800, from about 200 to about 500, from about 200 to about 400, from about 300 to about 400, from about 350 to about 450, about 200, about 250, about 300, about 350, about 400, about 450, about 500, about 550, about 600, about 650, about 700, about 750, about 800, about 850, about 900, about 950, about 1000 Daltons, etc. In some embodiments, the PEG can be present in the composition in an amount of from about 0.1 to about 20 wt % of that of the total composition. For example, the PEG can be from about 0.2 wt % to about 10 wt %, or from about 0.5 wt % to about 10 wt %, or from about 1 wt % to about 10 wt % of the total composition.

Other non-ionic hydrophilic material such as copolymers of PEG and PPG (polypropylene glycol), e.g., poloxamers, can also be used. In one example, Poloxamer-188 (which has an average molecular weight of about 8400 Daltons) can be used.

In some embodiments, the composition further comprises pharmaceutical carriers or excipients compounds or materials which enable the compositions to be presented in topically administrable semi-solid aqueous gel forms. For example, carboxymethylcellulose can be used as a gel-forming agent. However, other cellulose derivatives such as microcrystalline cellulose as well as polysaccharides such as alginate and agarose, tragacanth, guar gum, xanthum gum, are also suitable as gel-forming agents. The gel may, if required, be made thicker and/or stiffer by addition of a relatively resilient gel-forming material such as a cross-linked fibrous protein, e.g. gelatin or collagen cross-linked with formaldehyde.

In some embodiments, the composition can be in a form of a cream, which can include those excipients suitable for a cream formulation, such as paraffin oil, vaseline, wax, organic esters such as cetyl palmitate, etc.

In some embodiments, the composition of the invention further comprises a thickener for desired viscosity of the composition for skin delivery. For example, the thickener can include hydroxypropyl cellulose (HPC). HPC can make the composition into a smooth film for easy application. It also reduces evaporation and allows the wound to stay moist longer, a factor that has been shown to improve healing and result in decreased scarring. There are different grades of HPC available according to molecular weights or viscosity of certain concentrations of HPC water solution.

In some embodiments of the composition, XAV939 can constitute from about 0.001 wt % to about 5 wt % of the total composition (including water). In some embodiments, XAV939 can constitute from about 0.01 wt % to about 2 wt %, from about 0.02 wt % to about 1 wt %, or from about 0.05 wt % to about 0.5 wt % of the total composition. In some embodiments, GO-HA constitutes from about 0.001 wt % to about 5 wt % of the total composition. In some embodiments, GO-HA can constitute from about 0.01 wt % to about 2 wt %, from about 0.02 wt % to about 1 wt %, or from about 0.05 wt % to about 0.5 wt % of the total composition.

In the compositions as described herein, other pharmaceutical or therapeutic compounds may be included in addition, or as an alternative, to XAV939. In other words, the compositions with XAV939 present or with XAV939 removed can also serve as a base dispersion medium in which other pharmaceutical or therapeutic agents, especially those which are hydrophobic, may be dispersed, e.g., for topical administration to treat wound. These agents may include antifibrotic compounds such as pirfenidone, halofuginone, nintedanib, tocilizumab, rilonacept, etc., anti-cancer agents, anti-inflammatory agents, analgesics, antibiotics, etc.

In another aspect of the invention, a medical device is provided, which includes the composition as described herein, and a substrate upon which the composition is applied. The medical device can be in a form that facilitates topical administration of the composition, where the substrate can be constructed with suitable strength and flexibility for covering, securing and/or protecting the wound. For example, the substrate can be a patch, a pad, a tape, a bandage, a gauze, a suture, etc.

In yet another aspect of the invention, a method of treating a cutaneous or dermal wound in a subject (e.g., a human or a non-human animal) is provided. The method comprises contacting the wound with an effective amount of the composition as described herein. The wound can be a type where its normal healing is accompanied by scar formation. The wound can be a surgical wound that is caused by a physical impact that disrupts the structure and function of the skin (such as a laceration, abrasion, cut, scratch or puncture by a knife, scalpel, bullet, or other sharp or blunt objects). The wound can also be caused by excessive (low or high) temperature, such as a burn. The wound can also be a chronic wound that does not heal in expected time due to the lack of one or more of the main requirements of healing, including a good supply of blood, oxygen and nutrients, and a clean and infection-free environment. Examples of chronic wounds include ischemic wounds where the wound area is not getting sufficient blood supply. Diabetic ulcers are a common type of ischemic wounds.

The composition(s) of the present invention described herein can be administered by applying the composition(s) topically on the wound site. If the composition is included in a medical device described herein which includes a substrate such as a patch or a pad, the medical device can be secured to the wound site such that the composition contacts the wound.

In some embodiments, the method of treatment can include delivering a second wound medication or therapeutic agent to the subject, comprising one or more of: corticosteroid, a cytotoxic drug, an antibiotic, an antiseptic, nicotine, an anti-platelet drug, an NSAID, colchicine, an anti-coagulant, a vasoconstricting drug or an immunosuppressive, a growth factor, an antibody, a protease, a protease inhibitor, an antibacterial peptide, an adhesive peptide, a hemostatic agent, living cells, honey, or nitric oxide. These therapeutic agents can be delivered as separate dosage forms from the compositions described herein, or may be included as additional components of the compositions described herein, hence delivered together with XAV939.

In a further aspect, the present invention provides methods for preparing the compositions described herein and the intermediate compounds. In one embodiments, a method of preparing a GO-HA conjugate is provided, which includes: (a) modifying GO by converting at least some of the benzoxylic acid groups of the graphene oxide to terminal aliphatic carboxylic acid groups; (b) derivatizing HA by reacting HA with a reagent having dual functional groups reactive to the terminal aliphatic carboxylic acid groups, the dual functional groups being intervened by a spacer group; and (c) reacting the modified GO obtained in (a) and derivatized HA obtained in (b), thereby forming a GO-HA conjugate.

In the above preparation method, the spacer group can be an unsubstituted or substituted, saturated or unsaturated linear alkylene group having 2-20 backbone carbons. For illustration and not limitation, the reagent for derivatizing HA can be selected from the following:

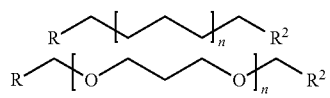

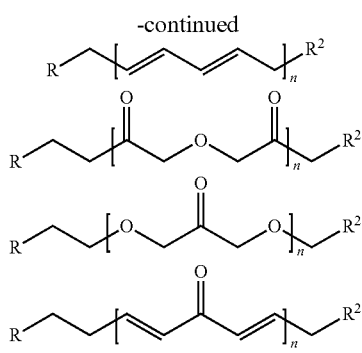

where $R^1$ and $R^2$ can be independently —$CONHNH_2$, —SH, —$NH_2$, —OH, or other nucleophiles, and n is an integer and can be for example, 1-20, e.g., 1, 2, 3, 4, 5, 6, 7, 8, 9, 10, etc. In some embodiments, the reagent for derivatizing HA can be a dihydrazide, such as adipic acid dihydrazide.

In some embodiments, a method for preparing a composition of the present invention includes: obtaining GO-HA (e.g., by the methods above), dissolving the GO-HA conjugate in water to obtain a GO-HA water solution, and adding XAV939 to the GO-HA water solution to form a mixture. In some examples, this is accomplished by dissolving XAV939 first in a non-ionic hydrophilic polymer, e.g., PEG-400 (or PEG 400, having an average molar mass of about 400), and then the XAV939 solution is added into the GO-HA conjugate water solution.

The present invention provides a wound treatment strategy that simultaneously addresses several facets of wound healing by synergistically combining a multi-functional scaffold (GO) conjugated to a highly hygroscopic material (HA) traditionally beneficial in wound healing, and aqueous solubilization of a potent Wnt pathway inhibitor (XAV939) for improved healing of cutaneous wounds with reduced scarring. Without wishing to be bound by any particular theory, it is believed the compositions and methods of the present invention can prevent, reduce, or inhibit dermal fibrosis and scarring in wound healing by inhibiting TNK1 and 2 via XAV939 targeting the Wnt/β-catenin in the skin, thereby directing wound healing toward a regenerative process rather than a fibrotic process. It is believed that XAV939 is coated onto the GO as a nanocarrier due to the ability of GO to complex (via π-π interactions) hydrophobic compounds, and with the hydrophilic HA linked to GO, rendering the hydrophobic compounds "water soluble". Also, GO may serve as a scaffold for cell growth and communication due to its good biocompatibility, and properties that influence cell-cell-communication, cell division and cell fate, as well as possible suppression of microbes.

Additional benefits of the topical composition and topical administration of embodiments of the present invention is low toxicity and high bioavailability of the beneficial components to the site of injury/wound.

The following examples are provided for purpose of illustration of certain aspects of the description herein and should not be deemed to limit the invention in any way.

The instrumentation used in the Examples: FT-IR: Thermo Nicolet 380 FT-IR with a SmartOrbi Diamond ATR accessory; 1H NMR: 500 MHz Bruker DRX500 or AV-500 NMR spectrometer; UV-Vis: Shimadazu Pharma Spec UV1700. Solvents: 99% pure, supplied by Sigma-Aldrich; Sonication was conducted at 42 kHz in a bath sonicator.

Example 1: Modification of GO

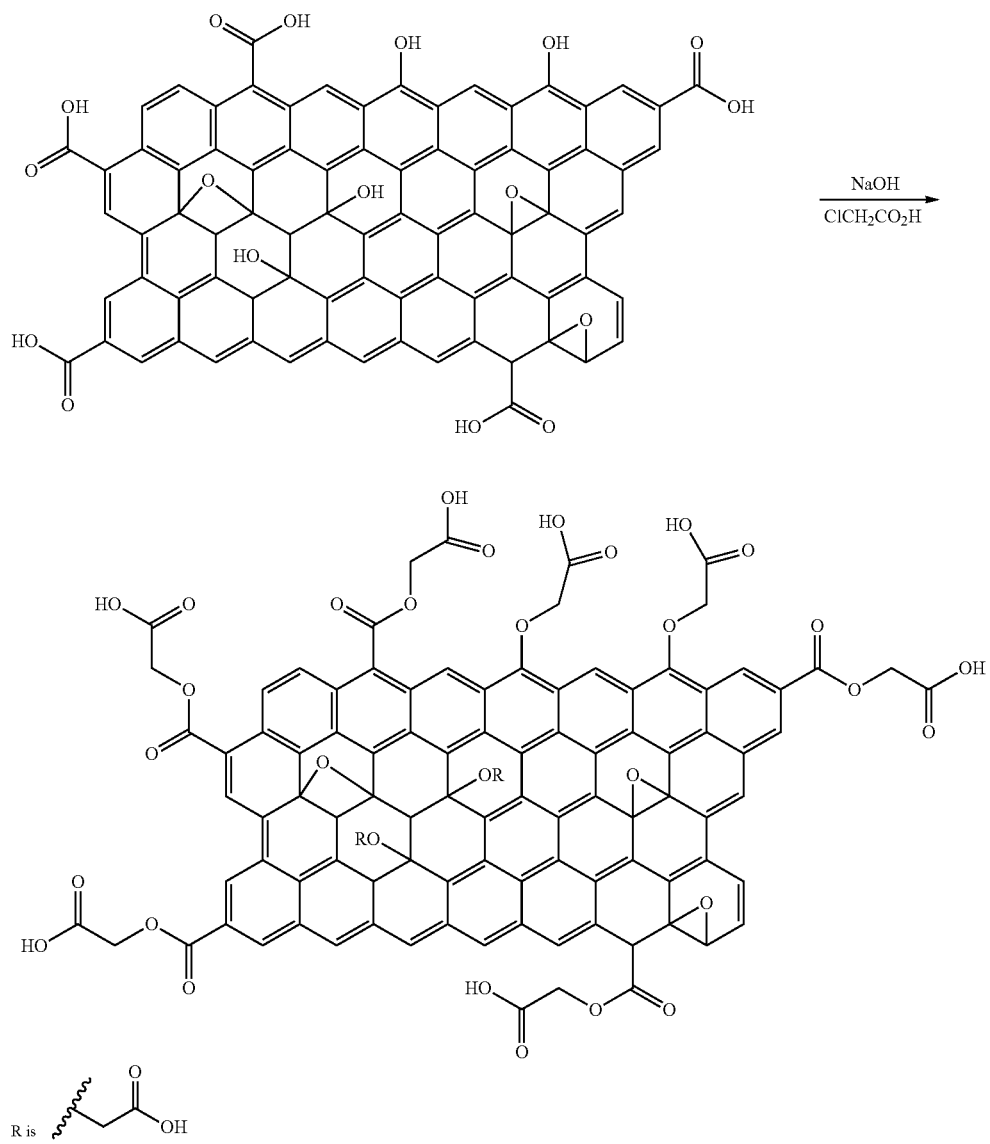

Although GO includes many carboxylic acid groups on its edges, the reactivity of these aromatic carboxylic acid groups is not high. To improve its linking efficiency with HA, some of these aromatic carboxylic acid groups on GO are converted to aliphatic aromatic carboxylic groups. See Scheme 1. In this step, some hydroxyl groups of GO are also converted to carboxylic groups (as illustrated above).

Graphene oxide (1.25 g, 250 mL of 5 mg/mL GO dispersion in de-ionized water; supplier: Goographene Inc.) was added to 250 mL of ultra-pure de-ionized water and stirred for 5 minutes. Sodium hydroxide pellets (3 g (0.075 moles); supplier: Sigma-Aldrich) were added in small solid portions to the mixture over 30 minutes. Once addition was complete, it was stirred for 1 hour at room temperature. Next the solution was ultrasonicated for 30 minutes, and then chloroacetic acid (3.54 g (0.0375 moles); supplier: Alfa Aesar) was added in small, solid portions over 20 minutes. The reaction mixture was then stirred for 18 hours at room temperature. The reaction mixture was acidified with hydrochloric acid (7 mL, 12N). The solution was then transferred to centrifuge tubes and centrifuged for 15 minutes at 5,000 rpm. The water layer was then decanted and more ultra-pure deionized water (~30 mL) added to the tubes before re-centrifugation. This process was repeated 3 times. Methanol (~30 mL) was added to the precipitated, modified graphene oxide remaining in the centrifuged tubes and centrifuged at 5,000 rpm for 15 minutes. This process was repeated 3 times. Once the methanol was decanted, the tubes were put under vacuum for 48 hours at room temperature for drying. A total of 0.926 g of modified graphene oxide was obtained. $^1$H NMR (500 MHz, $D_2O$) δ: 4.173 (—$CH_2CO_2H$) ppm (diagnostic peak). FT-IR: 1593 $cm^{-1}$, (C=C), UV-Vis λ: 268 nm.

Example 2: Derivatization of HA

Scheme 2

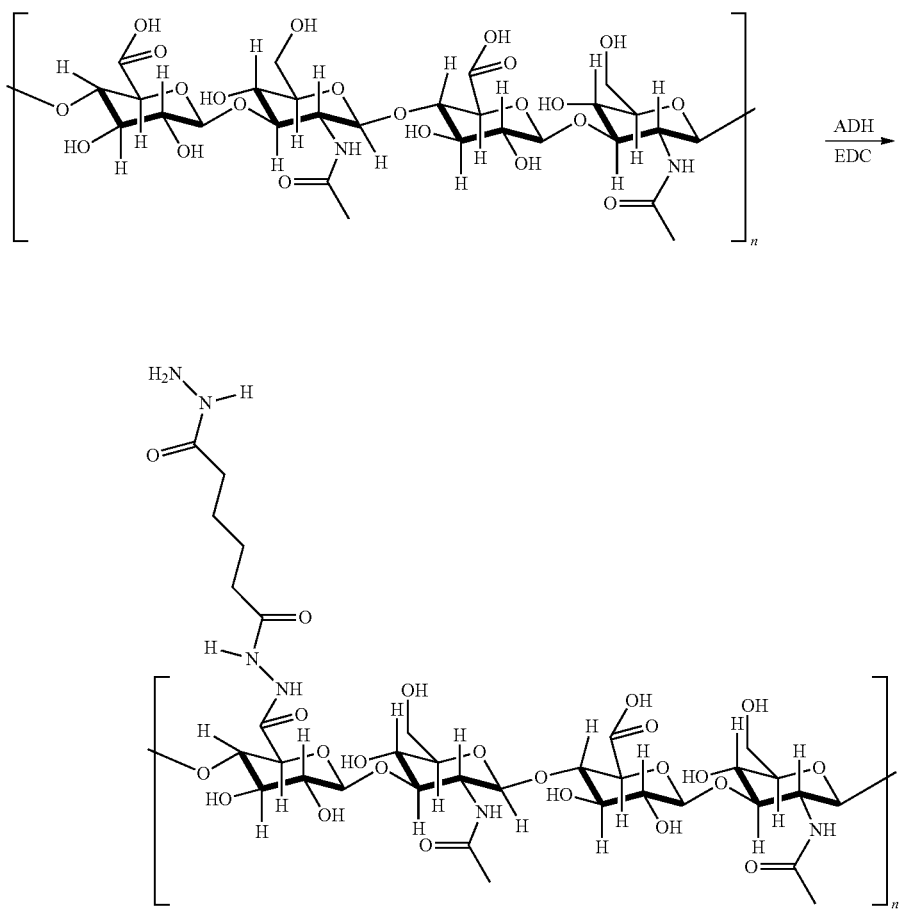

The general procedure of derivatizing HA is shown in Scheme 2. Hyaluronic acid (100 mg, MW=10,000 (n=13.5 in the scheme), 0.00001 moles; supplier: Creativepegworks) in ultra-pure deionized water (20 mL) was stirred for 5 minutes at room temperature. 1-(3-Dimethylaminopropyl)-3-ethyl carbodiimide hydrochloride (EDC) (52 mg, 0.00027 moles, supplier: Alfa Aesar) was added to the mixture and stirred for 3 hours at room temperature. During this time, the pH of the solution was maintained at approximately 5 to 6 by small additions of 0.1N hydrochloric acid. This mixture was added dropwise to a separate mixture containing adipic dihydrazide (ADH) (17 mg, 0.00027 moles; supplier: Alfa Aesar) in 5 mL of ultra-pure deionized water at room temperature. Once the addition was complete, it was stirred at room temperature for 18 hours. The solution was then subjected to dialysis (MWC=3500) for 24 hours. The mixture was then lyophilized to obtain a white powder (100 mg). $^1$H NMR (500 MHz, D$_2$O) δ: 2.4 (2H), 2.26 (2H), 1.66 (4H) ppm (diagnostic peaks). The substitution/loading degree was determined by the ratio of methylene hydrogens of adipic hydrazide to acetyl methyl protons of the Hyaluronic acid moiety. Integration indicated 30% coupling, resulting in approximately 8 substitutions. Coupling ranges were commonly 6-30%. A 6% coupling resulted in ~1.6 carboxyl units substituted.

Example 3: Reaction Between Modified GO and Derivatized HA to Prepare GO-HA Conjugate The general procedure of preparing GO-HA is outlined in Scheme 3 below. The modified GO obtained in Example 1 (0.90 g) was added to ultra-pure deionized water (100 mL) and stirred for 5 minutes, followed by ultra-sonication for 15 minutes. 2-Succinimido-1,1,1,3-tetramethyluronium tetrafluoroborate (TSTU) (0.32 g, 0.001 moles; supplier: Alfa Aesar), 2-(1H-benzotriazol-1-yl)-1,1,3,3-tetramethyluronium hexafluorophosphate, Hexafluorophosphate Benzotriazole Tetramethyl Uronium (HBTU) (0.41 g, 0.001 moles; supplier: Aldrich) and diisopropylethyl amine (DIEA) (0.15 mL, 0.001 moles; supplier: Sigma-Aldrich) was added to the mixture at room temperature and stirred for 5 minutes. Then a solution of hyaluronic acid-adipic hydrazide (obtained from Example 2) (0.90 g in 150 mL of ultra-pure deionized water) was added dropwise to the activated graphene oxide solution at room temperature. The reaction mixture was allowed to stir for 18 hours and then subjected to dialysis (MWC=20,000) for 2 days. The solution was then lyophilized to yield a black powder (1.13 g). $^1$H NMR (500 MHz, D$_2$O) δ: 1.94 (2H), 1.90 (2H), 1.21 (4H) ppm (diagnostic peaks).

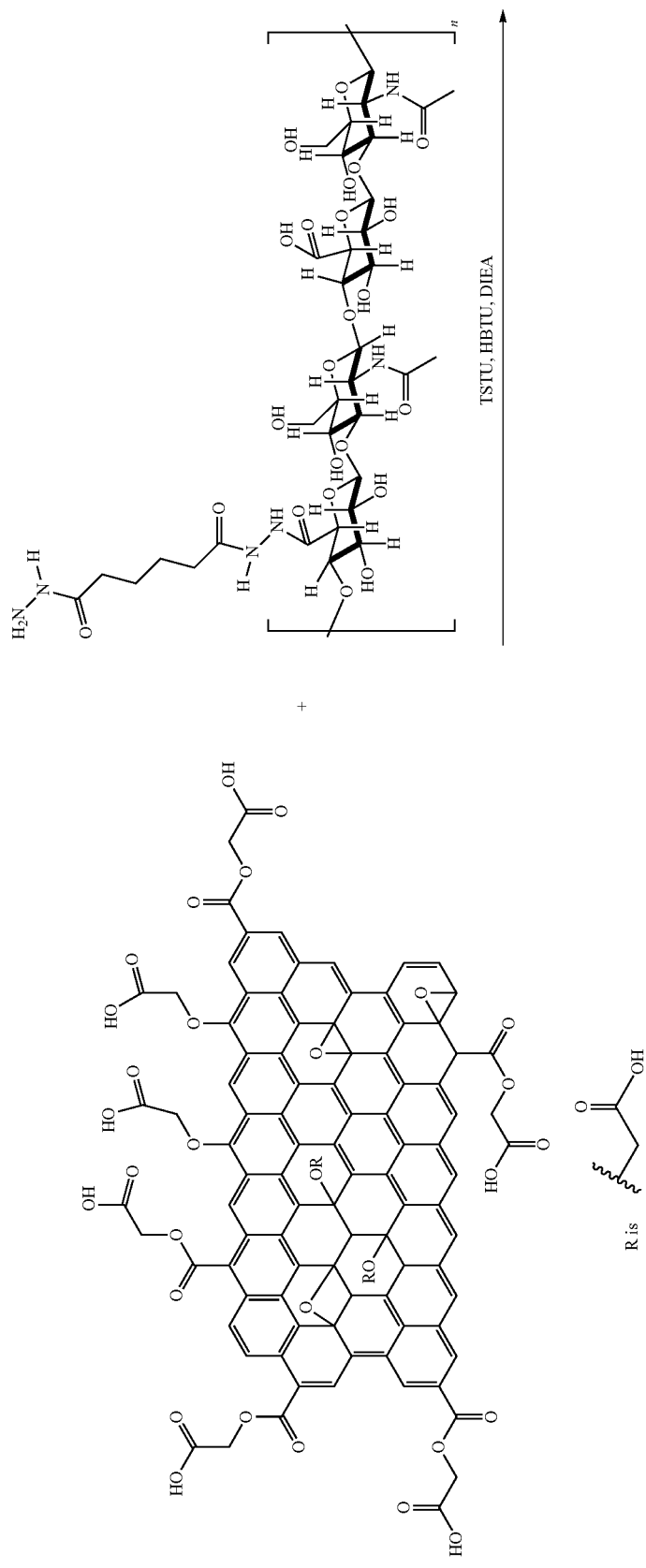

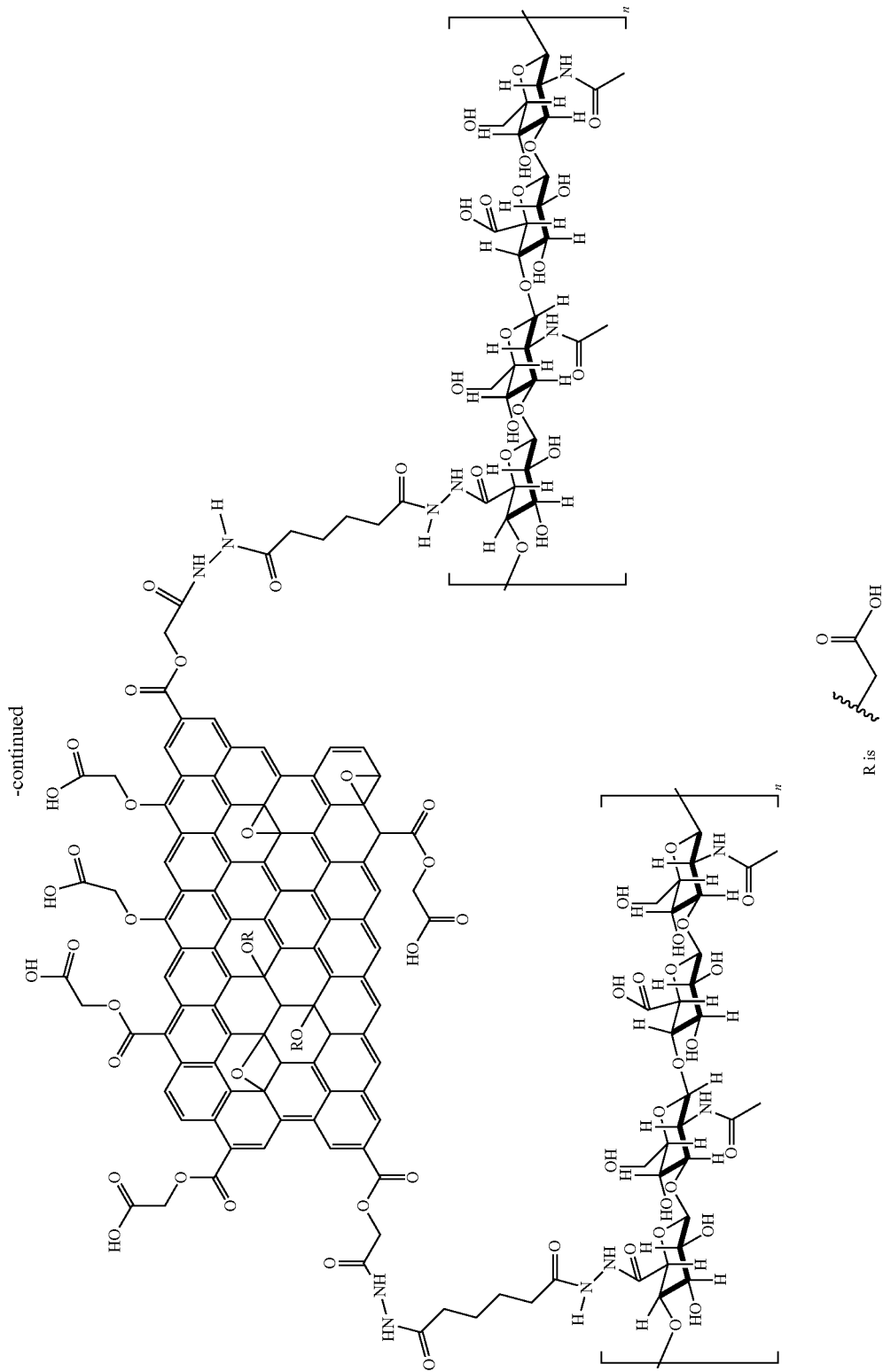

Example 4: Preparation of Wound-Treating Composition

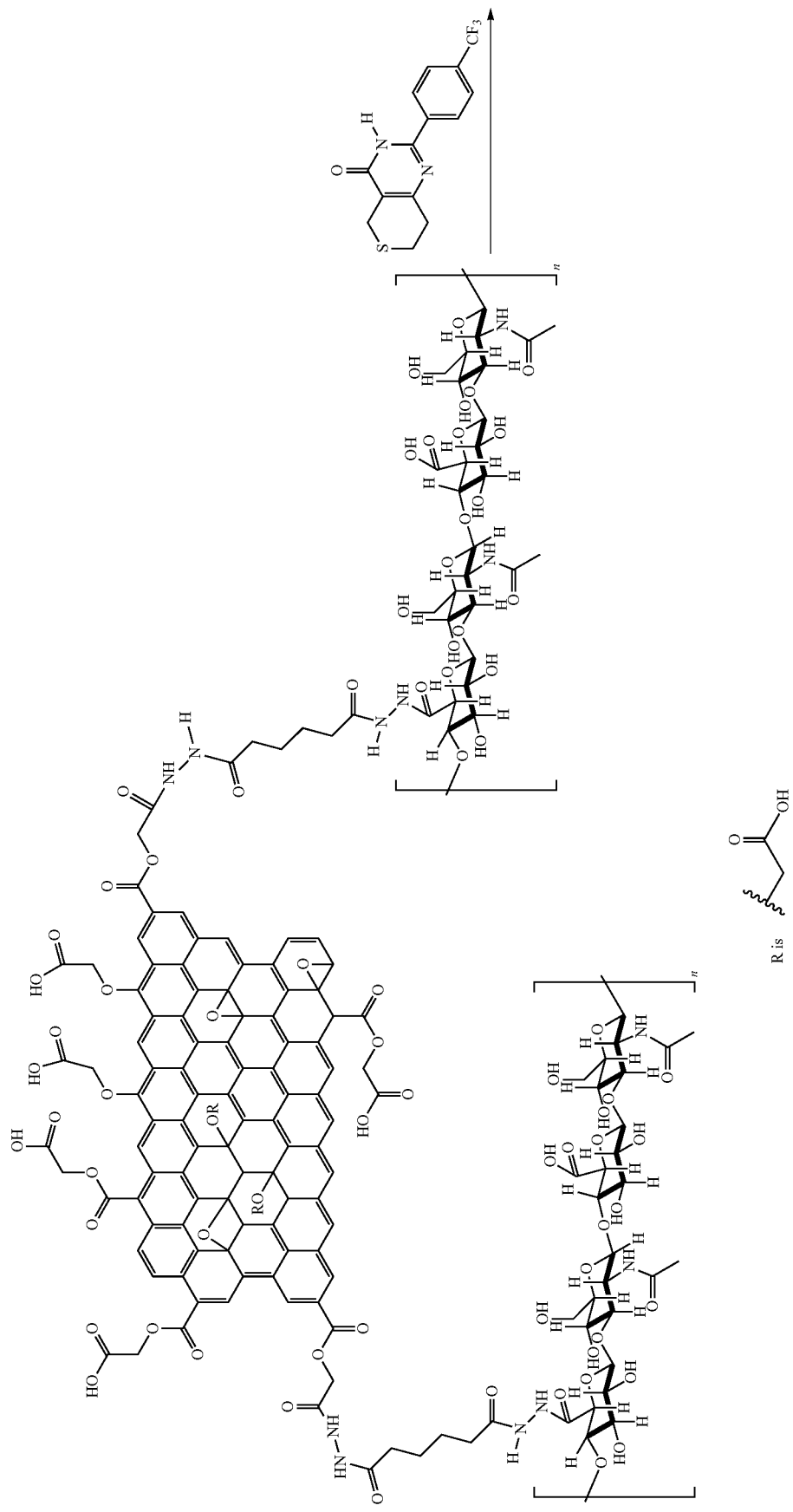

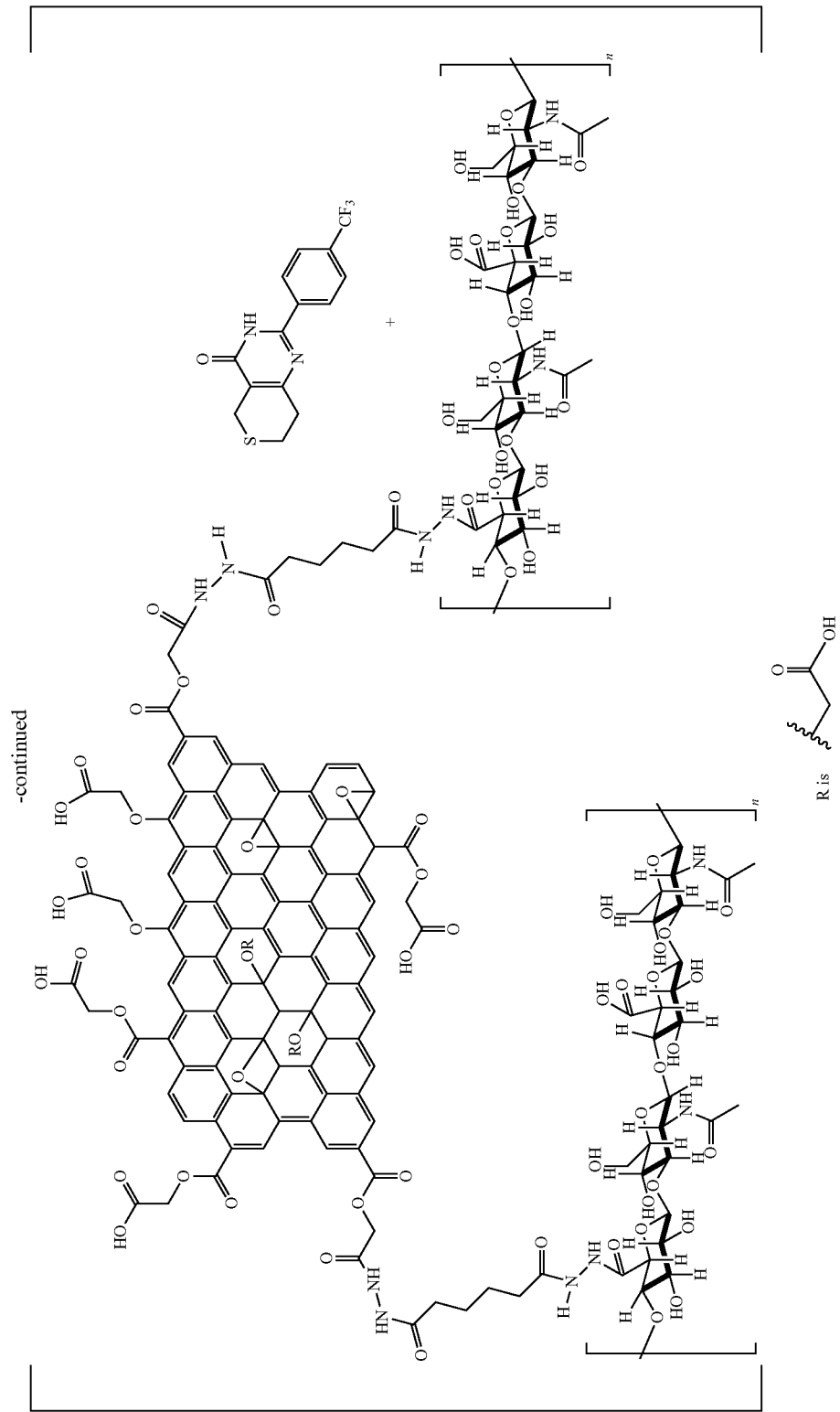

The procedure of preparing the composition is schematically shown in Scheme 4. 11 mg of the GO-HA obtained in Example 3 was dissolved in 11 mL of ultra-pure water, to create an effective concentration of 1 mg/mL. The solution was ultrasonicated for 10 minutes. XAV939 (11 mg; supplier: APEBIO) was added to PEG-400 (0.5 mL) and subjected to ultrasonication for 30 minutes. The XAV939 PEG-400 solution was added dropwise to the GO-HA and vigorously stirred for 5 minutes. The combined solution was then subjected to ultrasonication for 1 hour and then stirred at room temperature for 18 hours. Hydroxypropyl cellulose (0.2 g; supplier: Sigma-Aldrich) was added in small portions at room temperature with vigorous stirring. Once addition was complete, the solution was stirred at room temperature for 24 hours to form a viscous solution of the GO-HA/XAV939 complex. The complex was to be used as is.

Example 5. Animal Study 1

The objective of this study was to observe the wound healing effect of a composition of the present invention (STM42) in a dermal full thickness injury rat model following topical administration.
5-1: Test Article
STM42: the composition made according to the procedure described in Example 4.
Vehicle: 96 vol % water and 4 vol % PEG-400.
5-2 Animal Husbandry
16 Sprague-Dawley rats at age of about 6-8 weeks were used. Animal room was set to maintain a temperature of 23±2° C., humidity of 40-70%, and a 12-hour light/12-hour dark cycle. SPF Rat Growth Breeding Feed was provided ad libitum throughout the in-life portion of the study. Reverse Osmosis water was available to the animals ad libitum. Animals were free to access both food and water during the whole course of study.
5-3 Animal Grouping and Test Procedure
Animals were housed 5 rats per cage and acclimated for 5-7 days. They were then each anesthetized with pentobarbital sodium (45 mg/kg, ip., 2% in saline) and shaved on both sides of the back with an electric clipper, disinfected by applying betadine followed by 70% ethanol wiping. A (3 to 4 $cm^2$) full thickness of elliptical excision wound was created using toothed forceps, Acupunch® (12 mm, Acuderm Inc, USA) and scissors, skin was removed from the underlying muscle.

The animals were allocated to two groups according to the wound areas and body weight. Each group consists of 8 animals. Vehicle group: G1 (G1-1, G1-2, G1-3, G1-4, G1-5, G1-6, G1-7, G1-8); STM42 group: G2 (G2-1, G2-2, G2-3, G2-4, G2-5, G2-6, G2-7, G2-8). The grouping is summarized below.

| Group | Number of animals | Treatment | Dosage (μL/rat) | Route of Adm. | Dosing Schedule |
|---|---|---|---|---|---|
| 1 | 8 | Vehicle | 100 | Topical | QD × 14 d |
| 2 | 8 | STM42 | 100 | Topical | QD × 14 d |

STM42 and vehicle were topically administered to the animals respectively via a syringe to drip the formulation directly into the wound bed to create an even and consistent layer over the wound to cover all of the wound area. The treatment was continued daily for 2 weeks (14 days) following injury.

The animal body weight was measured twice weekly. Wound area boundary was drawn on a transparency paper with a permanent marker on Day 1, Day 5, Day 10 and Day 15 and the area will be measured with ImagePro Premier®. Photos of the wound of each rat were taken on Day 1, Day 5, Day 10 and Day 15.

For HE staining: Two 5 um slides per wound was stained with H&E and Masson's Trichrome and digitally scanned for pathology analysis. The pathology analysis included: (1) Evaluation of Scar resolution and rete ridges formation (dermal-epidermal junctions) in healing skin: Create Massons trichrome stained sections of skin from the full-thickness excisional wounds and evaluate "linear" extracellular matrix (scar-like) for all articles. (2) Evaluation of fiber thickness of healing skin by Massons trichrome stained sections imaged with circular polarized light for each article. (3) Evaluate rete-ridge for each article by H&E staining for each article.
5-4 Pathology Testing:
Materials: Skin samples, 10% formalin, hematoxylin, Eosin staining solution, acid fuchsin, Aniline Blue, dimethylbenzene, 70% alcohol, 95% alcohol, 100% alcohol, etc.
Instruments: Tissue hydroextractor (Shandon Excelsior ES™ Tissue Processor Fisher/Thermo A78400006); Tissue Embedder (Shandon Histocentre™ 3 Tissue Embedding Center Fisher/Thermo B64100010); Leica automatic slicing machine (Leica RM2255); Automatic staining machine (Automatic Slide Stainer Fisher/Thermo A74200010, Shandon Varistain® 24-4)
Tissue processing & slicing: (1) Tissue processing by tissue hydroextractor: gradient alcohol dehydration, transparentizing by dimethylbenzene, paraffin infiltration, embedding. (2) The samples are cut into 5 μm thick slides by Leica automatic slicing machine (3) H&E staining, Masson staining.

Evaluation parameters: re-epithelialization, neovascularization, Rete Ridge, scabbing, granulation. Scoring criteria are summarized in the below table:

| | 1. Re-epithelialization |
|---|---|
| New epithelium attempting to bridge over the wound gap | 0 No ingrowth of epithelium into the wound gap<br>1 Small stumps of growth from the edge<br>2 Large gap between the bridging epithelium<br>3 Small gap between the bridging epithelium<br>4 Complete bridging over the wound |
| | 2. Neovascularization |
| Newly formed vascular network in the wound bed | 0 Relatively normal<br>1 Mildly increased in number in the wound bed<br>2 Moderately increased in number in wound bed<br>3 Moderately to markedly increased in number in wound bed<br>4 Markedly increased in number in wound bed |
| | 3. Rete-ridge |
| Newly formed columns of epithelium extending downward to dermis of the wound bed | 0 No formation of rete ridge<br>1 Few columns formed<br>2 Mildly increased in number<br>3 Moderately increased in number<br>4 Markedly increased in number |
| | 4. Scabbing |
| Formation of scab on the cornified layer or on the wound bed | 0 Relatively normal<br>1 Small amount of scabbing<br>2 Moderate amount of scabbing<br>3 Moderate to marked amount of scabbing<br>4 Marked amount of scabbing |
| | 5. Granulation |

| | |
|---|---|
| Accumulation of inflammatory cells in the matrix of fibrotic/scar tissues in the wound bed of dermis | 0 Relatively normal<br>1 Small amount scattered in the wound bed<br>2 Moderate amount across the wound bed<br>3 Dense fibrotic tissues with heavy infiltration of inflammation<br>4 Fibrinoid formation in the dermis |

5-5 Observation & Analysis

Clinical signs: all clinical signs were recorded for individual animals, once before commencement of treatment and once daily during the study; observations were performed at the same time interval each day.

Terminal Studies: Animals in extremis or disposed for humane reasons and those that have completed the scheduled test period would be euthanized by carbon dioxide.

Statistical Analysis: The results (individual and group) were analyzed using Student's unpaired t-test. Data were given as Mean±SD or Mean±SEM. P<0.05 was considered significant.

5-6 Results

Clinical signs: Mortality, morbidity and the abnormal behavior were not found during the treatment period of the experiment. During the course of the experiment, the following signs did not occur: suffering (cachexia, weakening, difficulty to move or to eat, pain, cryings); toxicity (hunching, convulsions); 25% body weight loss for three consecutive days or 20% body weight loss on any day. There was no significant difference between groups in wound areas during the experiment (p>0.05).

On Day 15, 3 rats in each group (vehicle group: G1-4, G1-5, G1-8; STM42 group: G2-3, G2-4, G2-6) with an average wound healing rate were euthanized with carbon oxide, and wound tissue were excised and fixed neutral formalin buffer then embedded in paraffin for histology.

The scores of the STM42 group and the vehicle group are represented in FIG. 1. From FIG. 1 it can be seen that STM42 had a significant effect on re-epithelization (essential component of wound healing used as a defining parameter of a successful wound closure), improved neovascularization (the natural formation of new blood vessels, usually in the form of functional microvascular networks, capable of perfusion by red blood cells, that form to serve as collateral circulation in response to local poor perfusion or ischemia), improved rete ridge formation (epithelial extensions that project into the underlying connective tissue in both skin and mucous membranes-improved rete ridge formation is a sign of tissue regeneration rather than fibrosis/scarring (reduced rete ridge formation)), decreased scabbing (wounds with scabs take longer to heal and a sign of fibrosis/scarring) and decreased granulation (granulation tissue is composed of extracellular matrix proteins such as fibrin and type III collagen that can be quickly laid down by the initial surge of fibroblasts that is recruited to the wound site-causing a scar).

The total effect of STM42 toward wound healing with scar reduction can be evaluated using the following formula: Total=(Re-epithelization+Neovascularization+Rete ridge formation)−(Scabbing+Granulation)). Using mean measured values for each category: STM42=4.66. Vehicle=− 1.33. Under this metric, there is a 5.99-fold increase in scar reduction using STM42 in this study as compared to the control group.

Example 6. Animal Study 2

The objective of this study was to observe the wound healing effect of STM-52 in a dermal full thickness injury STZ induced diabetic rat model with topical administration.

6-1 Compound and Preparation

STM-52 (or STM52): same as STM42, the composition made according to the procedure described in Example 4.

Vehicle: 96 vol % water and 4 vol % PEG-400.

6-2 Test Article Preparation Procedure

Admixing the STM-52 well by sonicating for 10 minutes before injecting via syringe 100 uL of sample onto the wound.

6-3 Animal Husbandry 14 male Sprague-Dawley rats, grade SPF of an age of about 6-8 weeks were used. The rats had a blood glucose of >16.7 mM.

Weight at initiation of treatment: Within the range of 200~300 g.

Acclimation period: 7 days.

Environmental controls for the animal room were set to maintain a temperature of 23±2° C., humidity of 40~70%, and a 12-hour light/12-hour dark cycle. The 12-hour dark cycle may be temporarily interrupted to accommodate study procedures.

Food and water: SPF Rat Growth Breeding Feed (BEIJING KEAO XIELI FEED CO. LTD.) was provided ad libitum throughout the in-life portion of the study. Reverse Osmosis water was available ad libitum.

Animal selection and fasting: Animals to be used in this study were selected based on overall health and acclimation to caging. Animals were free to access both food and water during the whole course of study.

6-4 Experimental Design

Upon arrival at the animal facility, the animals were housed 5 rats per cage and acclimated for seven days. Prior to the experiments, food was withdrawn for about 16 hours. The rats were rendered diabetic by an i.p. injection of STZ (65 mg/kg) dissolved in sodium citrate buffer, pH 4.5. The rats with a final blood glucose level>16.7 mM (300 mg/dL) were included in the study. All the selected rats were anesthetized with pentobarbital sodium (45 mg/kg, i.p. 2% in saline) and shaved on both sides of the back with an electric clipper, disinfected by iodophor followed by 75% ethanol wiping. A (3 to 4 cm$^2$) full thickness of elliptical excision wound was created using Acupunch® (12 mm, Acuderm Inc, USA). The skin was removed from the underlying muscle using scissors and toothed forceps.

The animals were divided into two groups according to the wound area and the body weight.

| Group | Number of Animals | Treatment | Dosage (μL/rat) | Route of Adm. | Dosing Schedule |
|---|---|---|---|---|---|
| 1 | 7 | Vehicle | 100 | Topical | QD × 21d |
| 2 | 7 | STM-52 | 100 | Topical | QD × 21d |

The wound was topically administrated (via a syringe to drip the formulation directly into the wound bed to create an even and consistent layer over the wound making sure to cover all of the wound area) with STM-52 or vehicle (100 μL/rat). The treatment was continued daily for 21 days following injury.

Figure 2:
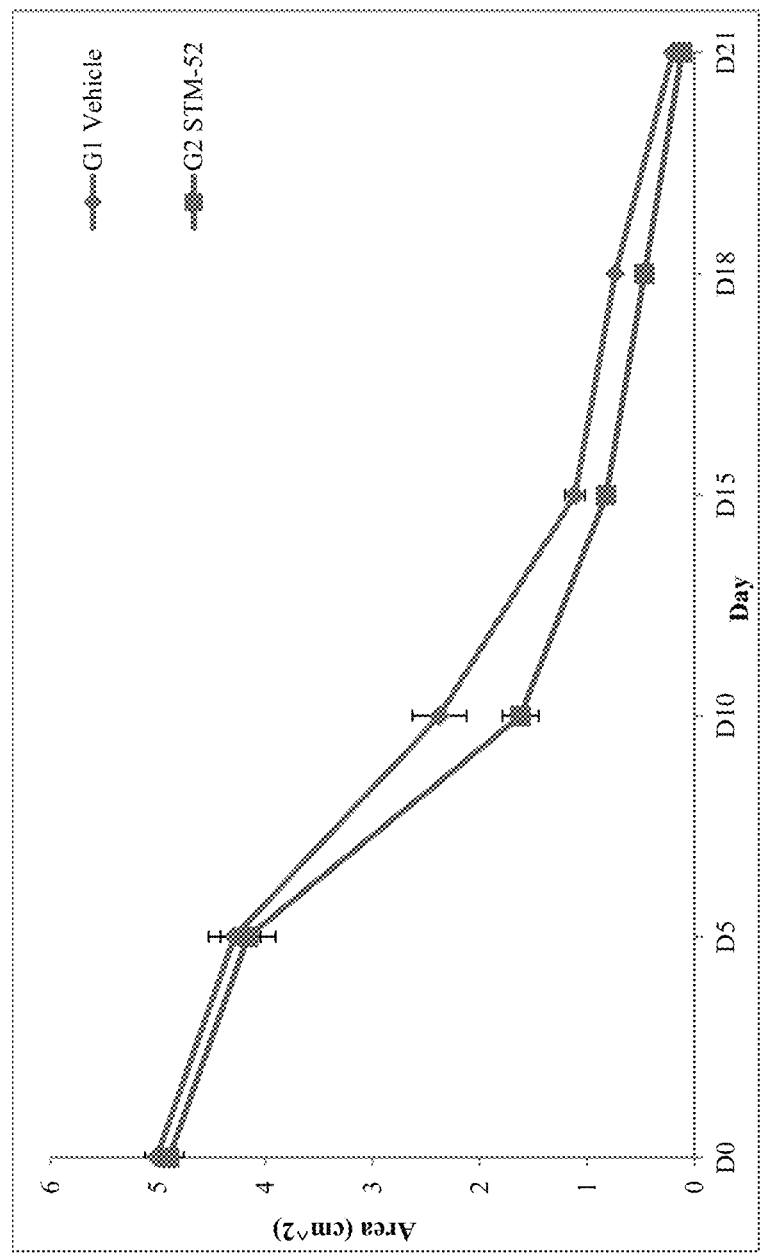
FIG. 2 is a plot showing the effect of a composition of the present invention on the wound healing of an animal model as compared to the effect of a vehicle composition.

FIG. 2 is a plot showing the average area size of the wounds of the Vehicle group and the STM-52 group during the course of the 21-day treatment. The results indicate that topical administration of STM-52 increased the rate of healing of the diabetic rat impaired healing animal model as compared to vehicle. Primarily, the rate increase was observed on days 10-18 of the 21 day study. Also during this time, there were no signs of overt toxicity as indicated by body weight measurements.

The word "about" as used herein in association with a numeric value or a numeric range mean "approximately" and refers to a result that can be obtained within a tolerance and the skilled person knows how to obtain the tolerance, for example, ±10% of the given value or range.

The term "effective amount" as used herein means the amount of a composition that, when administered to a subject for treating an undesirable or diseased condition (e.g., treating a wound) of the subject, is sufficient to ameliorate or improve such condition. The "effective amount" may vary depending on the composition, the condition and its severity, and the age, physical condition, and responsiveness of the subject to be treated.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, composition, device, system, article, material, kit, and/or method described herein. In addition, any combination of two or more such features, compositions, devices, systems, articles, materials, kits, and/or methods, if such features, compositions, devices, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A topical composition for treating a wound, consisting of:
    a matrix component consisting of a graphene oxide (GO) and hyaluronic acid (HA) conjugate (GO-HA), wherein the GO and HA are covalently linked via a linker;
    polyethylene glycol (PEG), where the PEG is optional;
    a thickener, where the thickener is optional;
    3,5,7,8-tetrahydro-2-[4-(trifluoromethyl)phenyl]-4H-thiopyrano[4,3-d]pyrimidin-4-one (XAV939); and
    water;
    wherein XAV939 constitutes from about 0.001 wt % to about 5 wt % of the total composition.

2. The topical composition of claim 1, wherein the PEG is present.

3. The topical composition of claim 2, wherein the PEG has a molecular weight of from about 200 to about 400 Daltons.

4. The topical composition of claim 2, wherein the PEG is in an amount of from about 0.1 wt % to about 20 wt % of the total composition.

5. The topical composition of claim 2, wherein the thickener is present.

6. The topical composition of claim 1, wherein the linker comprises 2-25 carbons.

7. The topical composition of claim 1, wherein the linker comprises one or more —$CH_2CH_2O$— units.

8. The topical composition of claim 1, wherein the linker comprises —IV—Rs—RY—, wherein IV and RY are each independently selected from the group consisting of —CO—, —COO—, —NH—, —NH—NH—, —NH—NH—CO—, —CS—, —S—, and —O—, and wherein Rs is an unsubstituted or substituted linear alkylene group having 2-20 backbone carbons.

9. The topical composition of claim 8, wherein IV and RY are each —NH—NH—CO—.

10. The topical composition of claim 1, wherein the weight ratio of XAV939 to GO-HA is from about 1:2 to about 2:1.

11. The topical composition of claim 1, wherein the GO-HA constitutes from about 0.001 wt % to about 5 wt % of the total composition.

12. A medical device comprising:
    a substrate; and
    the topical composition of claim 1 applied on the substrate.

13. The medical device of claim 12, wherein the substrate is a patch, a pad, a suture, a gauze, a tape, or a bandage.

* * * * *

UNITED STATES PATENT AND TRADEMARK OFFICE
CERTIFICATE OF CORRECTION

PATENT NO. : 11,291,730 B2
APPLICATION NO. : 16/153753
DATED : April 5, 2022
INVENTOR(S) : Daniel D. Holsworth It is certified that error appears in the above-identified patent and that said Letters Patent is hereby corrected as shown below:

In the Claims

In Claim 8, Line 31, the following formula "–IV–Rs–RY–" should read – –$R^x$–$R^s$–$R^y$– –;

In Claim 8, Line 31, "wherein IV and RY" should read – wherein $R^x$ and $R^y$ –;

In Claim 8, Line 34, "and -0-, and wherein Rs" should read – and -O-, and wherein $R^s$ –.

In Claim 9, Line 37, "IV and RY" should read – $R^x$ and $R^y$ –.

Signed and Sealed this
Eighteenth Day of October, 2022

Katherine Kelly Vidal
*Director of the United States Patent and Trademark Office*